(12) United States Patent
Ayala et al.

(10) Patent No.: US 10,241,103 B2
(45) Date of Patent: Mar. 26, 2019

(54) FOAM TESTING APPARATUS

(71) Applicant: Ayalytical Instruments, Inc., Chicago, IL (US)

(72) Inventors: Juan J. Ayala, Chicago, IL (US); Darren Bolgioni, Chicago, IL (US); Nikola Skulic, Bensenville, IL (US)

(73) Assignee: Ayalytical Instruments, Inc., Chicago, IL (US)

( * ) Notice: Subject to any disclaimer, the term of this patent is extended or adjusted under 35 U.S.C. 154(b) by 198 days.

(21) Appl. No.: 15/596,354

(22) Filed: May 16, 2017

(65) Prior Publication Data

US 2017/0328879 A1 Nov. 16, 2017

Related U.S. Application Data

(60) Provisional application No. 62/336,951, filed on May 16, 2016.

(51) Int. Cl.
*G01N 33/28* (2006.01)
*G01N 1/44* (2006.01)
*G01N 25/02* (2006.01)

(52) U.S. Cl.
CPC .......... *G01N 33/2888* (2013.01); *G01N 1/44* (2013.01); *G01N 25/02* (2013.01); *G01N 33/2805* (2013.01)

(58) Field of Classification Search
CPC .......... G01N 1/44; G01N 33/26; G01N 33/28; G01N 33/2888; F16N 2200/18

USPC .............................................. 73/53.05, 60.11
See application file for complete search history.

(56) References Cited

U.S. PATENT DOCUMENTS

| 2,315,983 | A | * | 4/1943 | Ross | B01L 3/00 73/60.11 |
| 4,426,879 | A | * | 1/1984 | Humphries | G01N 13/00 73/60.11 |
| 5,824,886 | A | * | 10/1998 | Selby | B01L 7/00 73/60.11 |
| 6,009,748 | A | * | 1/2000 | Hildebrandt | G01N 33/2888 219/523 |
| 8,490,464 | B1 | * | 7/2013 | Selby | G01N 7/14 73/19.1 |
| 2006/0162430 | A1 | * | 7/2006 | Leinemann | G01N 7/00 73/53.06 |

OTHER PUBLICATIONS

"Standard Test Method for Foaming Characteristics of Lubricating Oils"—ATSM Standard D892.*

* cited by examiner

*Primary Examiner* — Benjamin R Schmitt
(74) *Attorney, Agent, or Firm* — Olson & Cepuritis, Ltd.

(57) ABSTRACT

A foam testing apparatus with a closed loop air circulation along a sample cylinder which maintains a lubrication oil sample at a desired temperature during a test procedure. The apparatus may include a digital camera adjacent to the sample cylinder for observation and recording of foam characteristics during the test procedure.

20 Claims, 7 Drawing Sheets

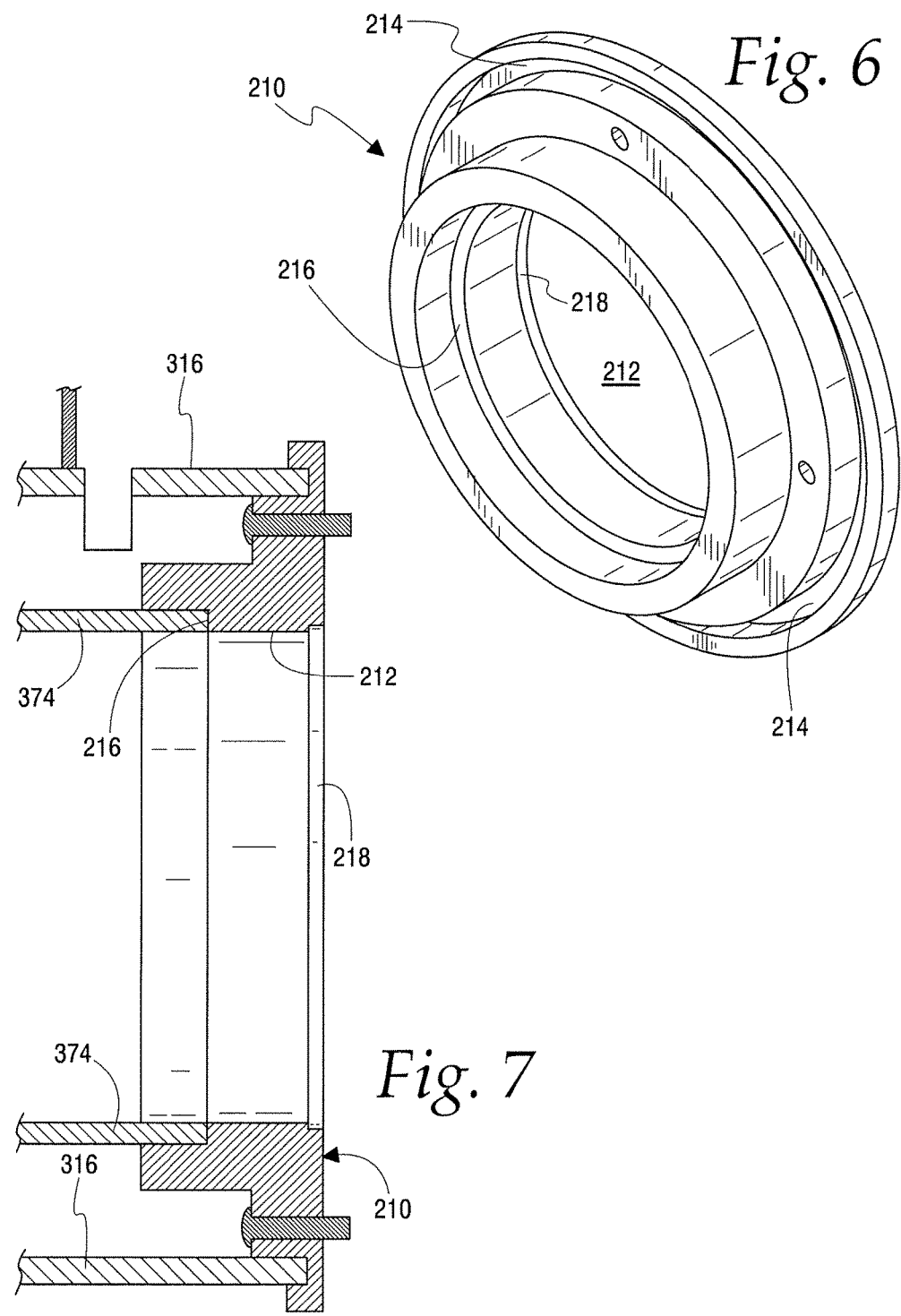

FOAM TESTING APPARATUS

CROSS-REFERENCE TO RELATED APPLICATIONS

This application claims priority benefit of U.S. Provisional Application Ser. No. 62/336,951, filed on May 16, 2016, the entire disclosure of which is incorporated herein by reference.

FIELD OF INVENTION

This invention relates to apparatus for testing foams, in particular to apparatus for testing the foaming characteristics of lubricants at elevated temperatures.

BACKGROUND OF INVENTION

Foaming is an important property of lubricating oils and the like automotive liquids. A tendency of a lubricant to foam adversely affects the lubricating properties of the oil by reducing oil circulation within an engine, possibly leading to losses of oil and enhancing oxidation. The tendency of an oil to foam at elevated temperatures can cause pump cavitation and is a serious problem also in splash lubrication, high speed gearing, and similar uses. Inadequate lubrication and overflow loss of lubricant are factors that can lead to premature mechanical failure.

Accordingly, for quality control purposes it is important to be able to evaluate the foaming tendencies of lubricating oils, hydraulic fluids, and the like.

While foam testing devices are known in the art and standards for foam testing, such as ASTM Standard D892, have been established and have undergone revisions from time to time, reliable foam measurements continue to be challenging. Existing foam testing devices continue to exhibit shortcomings such as bulkiness of the device, difficulty in operation, difficulty in handling oil samples to be tested, relatively long test period duration, reproducibility of test results.

The present invention provides an improved foam test apparatus that ameliorates the aforedescribed shortcomings, is compact, easy to use, and provides consistent, readily reproducible foam test results.

SUMMARY OF INVENTION

The foam testing apparatus efficiently measures the foaming characteristics of oil lubricants. Oil at predetermined temperatures is foamed by introducing air by means of a diffuser made of a ceramic, sintered stainless steel particles, and the like. The amount and quality of foam generated can be monitored by machine vision, visually, or both.

The apparatus utilizes a graduated sample cylinder equipped with a diffuser. Oil sample temperature is regulated by a heat lamp and a Peltier device which together maintain the desired sample temperature by gas (air or nitrogen) circulated around the sample cylinder, as well as by direct radiant heat from the heat lamp.

In particular, the foam testing apparatus comprises a base housing, an open-ended transparent housing cylinder on the base housing, an open ended, transparent, intermediate cylinder within the housing cylinder, and an elongated, transparent, graduated sample cylinder equipped with a gas pipe having a gas diffuser at the distal end of the pipe.

The base housing defines an enclosure with a top opening. The transparent housing cylinder is mounted to the base housing over the top opening. A heat lamp is situated in the enclosure defined by the base housing and under the housing cylinder.

A conical reflector is situated over the heat lamp and defines an open socket sized to receive the open-ended transparent intermediate cylinder.

Alternatively, the top opening in the base housing can be provided with a collar that supports the transparent housing cylinder as well as the transparent intermediate cylinder. The collar is mounted to the enclosure defined by the base housing and, in turn, defines a central passage for circulating gas, an internal shoulder around the passage for supporting the transparent intermediate cylinder, and an outer circumferential groove for receiving the transparent housing cylinder. An end portion of the open-ended transparent intermediate cylinder abuts the internal shoulder, and an end portion of the transparent housing cylinder is seated in the circumferential groove.

A recess can be provided on the underside of the collar around the central passage for mounting an illumination ring, e.g., a ring of light emitting diodes (LEDs).

An outer annular confined flow passageway is defined by the housing cylinder and the open-ended transparent intermediate cylinder.

The sample cylinder is positioned within the open-ended transparent cylinder, preferably suspended from a housing cylinder cap which closes the housing cylinder. The sample cylinder together with the open-ended intermediate cylinder define an inner annular confined flow passageway therebetween. The inner annular confined flow passageway is in flow communication with the outer annular confined flow passageway. The sample cylinder has a closed bottom portion and an open top portion. A gas pipe carrying the gas diffuser extends into the sample cylinder and is suspended from a sample cylinder cap which provides closure for the open end of the sample cylinder. A temperature sensor such as a thermistor, a thermometer, and the like extends into the space defined by the sample cylinder, and positioned to be in contact with the lubricating oil to be tested. A fan in the enclosure circulates gas through the confined flow passageways.

A closed loop gas, usually air, circulation system serves to maintain the oil sample to be tested at the desired temperature. The closed loop gas circulation system includes the internal annular confined flow passageway, the external annular confined flow passageway, a duct connecting the housing cylinder with the enclosure defined by the base housing, and a gas circulation fan which induces gas flow through the annular confined flow passageways. The heat lamp and an optional Peltier device are situated in a heat exchange relationship with the gas stream circulated through the enclosure.

In use, an oil lubricant sample is placed in the sample cylinder, the sample brought to and maintained at a predetermined temperature, and gas, usually air, at a predetermined flow rate is introduced into the sample through the diffuser while the volume and quality of generated foam is monitored and evaluated. During testing, external gas, i.e., air or nitrogen, at a predetermined temperature is circulated within the test apparatus by passing first through the inner annular passageway to transfer heat to the sample and then through the outer annular passageway. Circulated gas temperature is adjusted as deemed necessary using the heat lamp, the Peltier device, or both, based on sample temperature.

BRIEF DESCRIPTION OF THE DRAWINGS

In the drawings,

FIG. 6 is a perspective view of a collar that can be used to support a transparent housing cylinder and a transparent intermediate cylinder;

FIG. 7 is a sectional side view of the collar shown in FIG. 6 with lower end portions of the housing cylinder and the intermediate cylinder seated in the collar.

DESCRIPTION OF PREFERRED EMBODIMENTS

Figure 1:
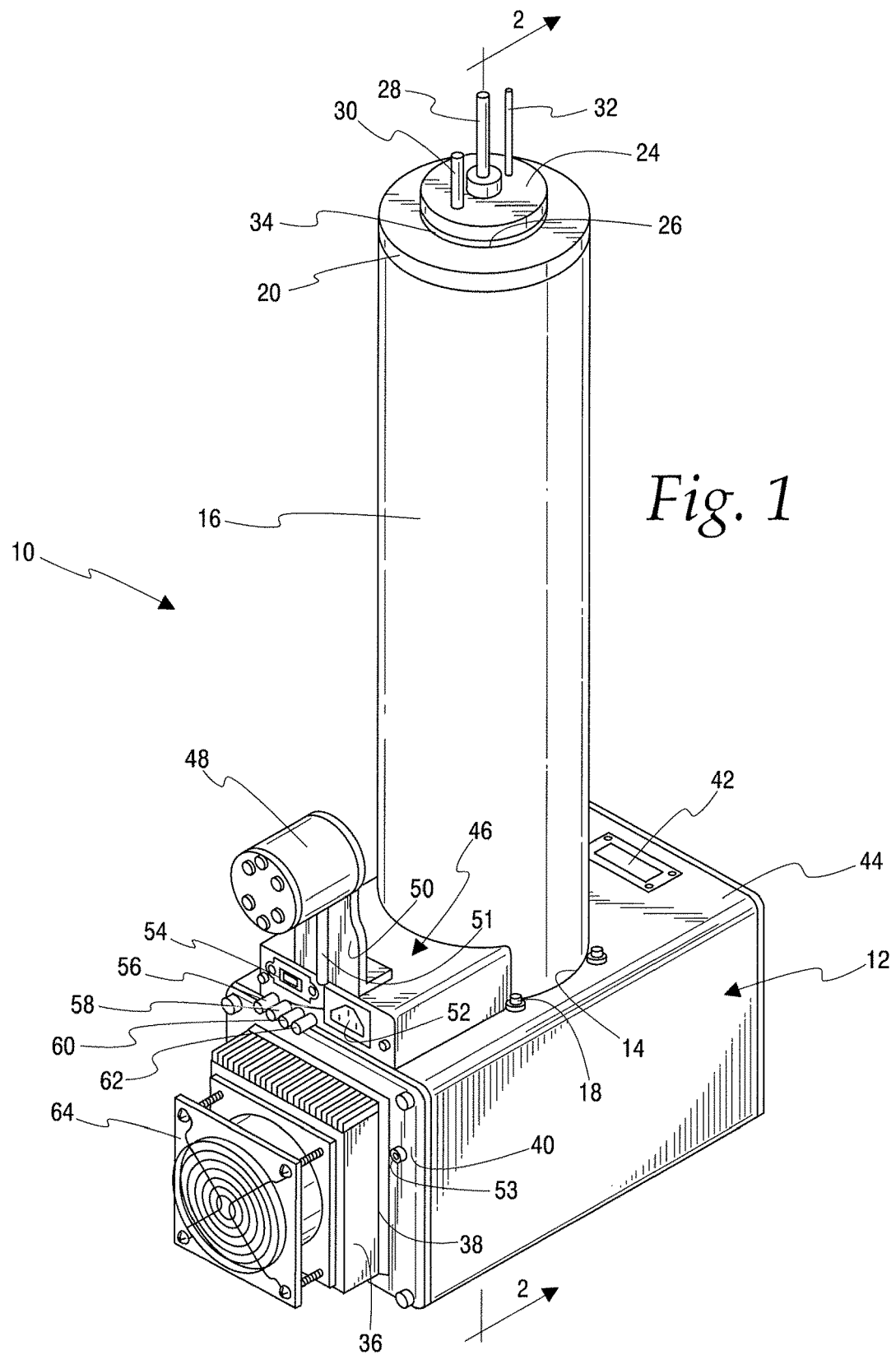
FIG. 1 is a rear perspective view of foam testing apparatus embodying the present invention.

In describing the preferred embodiments reference will be made to terms such as "upper," "lower," "top," "bottom," and the like. These terms are relative terms, and are utilized for ease of understanding the apparatus as illustrated in the drawings. It is to be understood that when the illustrated apparatus is in use, or is transported from one location to another, it may assume an orientation which is different but appropriate under the circumstances then existing.

Referring to FIG. 1, foam testing apparatus 10 has a base housing 12 which defines an enclosure 13 and top opening 14. Transparent housing cylinder 16 is open at both ends, and is mounted to base housing 12 over top opening 14. Housing cylinder 16 is held in place by head cap screws such as head cap screw 18.

Housing cylinder cap 20 is received in the top or upper end portion of housing cylinder 16 and provides an airtight seal. Transparent graduated sample cylinder 22 (FIG. 2), sealed by sample cylinder cap 24, is received in central aperture 26 defined by housing cylinder cap 20 and suspended from housing cylinder cap 20. Sample cylinder cap 24 is also provided with apertures that receive air pipe 28, temperature sensor port 30 and vent conduit 32. A sealing gasket, such as O-ring 34 and the like, provides an airtight seal between housing cylinder cap 20 and sample cylinder cap 24.

External heat exchanger 36 protrudes outwardly through opening 38 in rear panel 40 of base housing 12. Cooling fan 64 distributes air over external heat exchanger 36. Temperature display window 42 is provided in top panel 44. Cover 46 adjacent to housing cylinder 16 defines a duct or manifold 96 which provides air flow communication between housing cylinder 16 and enclosure 13 defined by base housing 12, a portion of which serves as plenum for an air circulation system within housing cylinder 16 as is discussed in greater detail hereinbelow.

Camera housing 48 is mounted above cover 46 by camera housing bracket 50. Digital camera 49 (FIG. 2) is provided in housing 48 for observation and recording of foam characteristics during a foaming test procedure. Camera housing bracket can hold housing 48 in a fixed position relative to transparent housing cylinder 16. Alternatively, bracket 50 can be adjustable in length, for example using a step motor (not shown), along the length of housing cylinder 16.

Camera cable 51 connects digital camera 49 within camera housing 48 to an image processing unit and digital signal processor (not shown) within base housing 12.

Power socket 52 together with fuse 53 (FIGS. 1 and 3) provide connection to an external power source for an air circulation fan, a cooling fan, controller, flow meter, mass flow meter, microprocessor, and the like, as well as for a heat lamp, LED illumination of sample, and the like. USB port 54 provides connection means for a communications bus for programming. Air tubes 56, 58, 60 and 62 are part of an air circulation system within test apparatus 10 described in detail hereinbelow. Peltier device 66 (FIG. 2) within base housing 12 provides thermoelectric cooling for circulated air.

Figure 2:
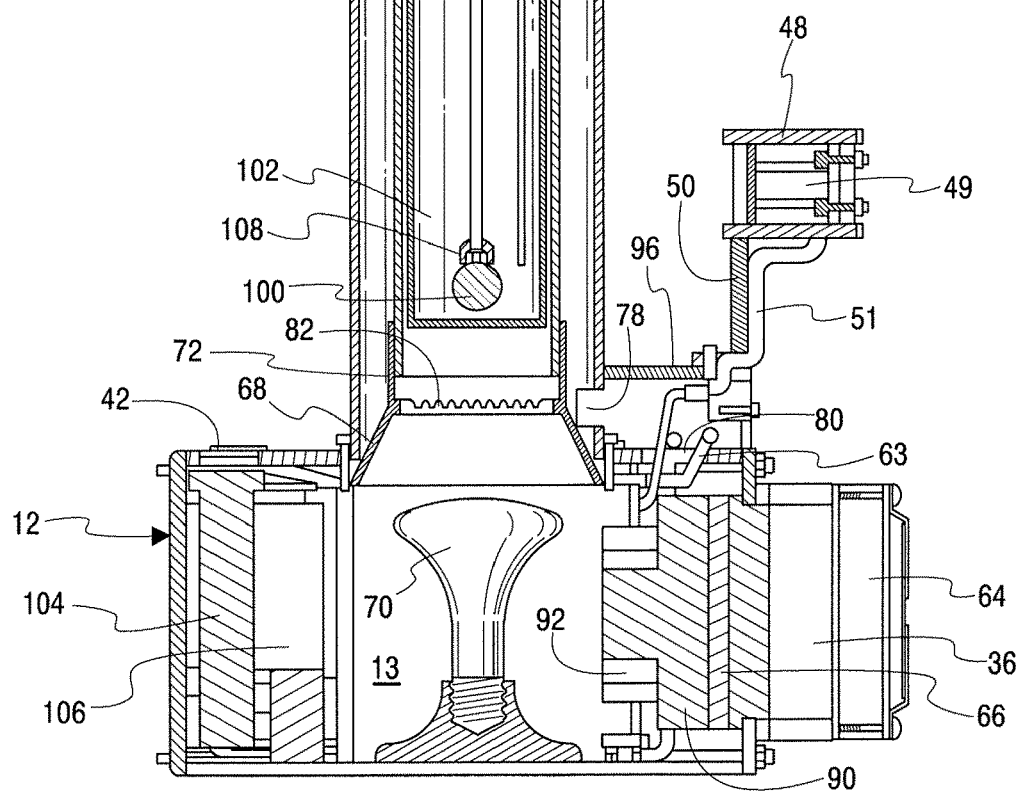
FIG. 2 is a side sectional view of the apparatus at plane 2-2 of FIG. 1.
Figure 3:
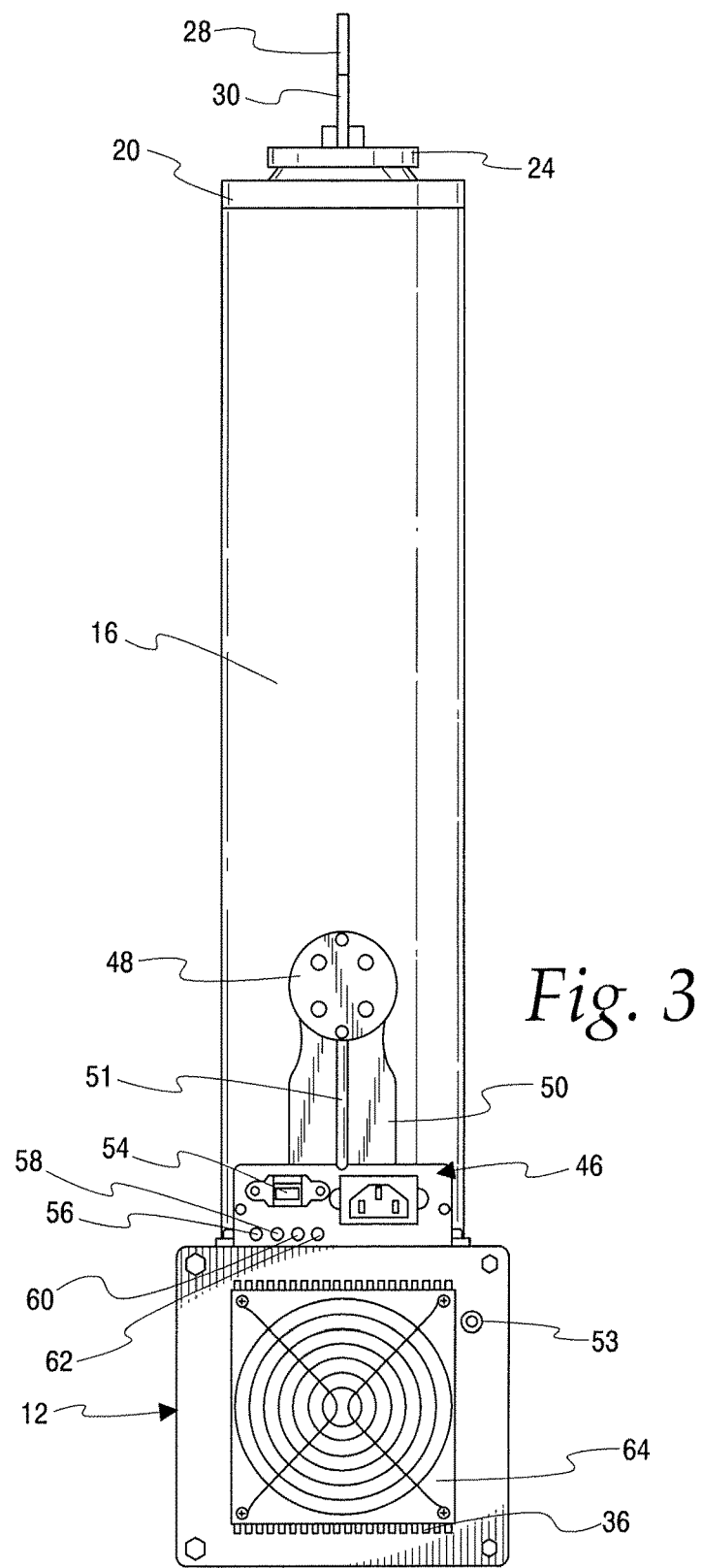
FIG. 3 is an end elevation view of the apparatus shown in FIG. 1.

As shown in FIG. 2, external heat exchanger 36 and associated fan 64 are on the hot side of Peltier device 66, and internal heat exchanger 90 with associated air circulation fan 92 are on the cold side of Peltier device 66. Heat lamp 70 and Peltier device 66 are in enclosure 13 adjacent to one another and in the path of air circulated through enclosure 13.

Peltier device 66 primarily serves to decrease temperature of circulating air as stated hereinabove. If desired, however, Peltier device 66 can also supply additional heat to the circulating air by reversing the direction of current. In such a case the normally cold side of Peltier device becomes its hot side, and vice versa.

Optional conical reflector 68 within the lower end portion of housing cylinder 16, situated over heat lamp 70, defines an open socket 72 unitary with conical reflector 68. Open-ended transparent intermediate cylinder 74 is positioned within housing cylinder 16 and is seated in open socket 72. Together with housing cylinder 16 open-ended transparent intermediate cylinder 74 defines outer annular confined flow passageway 76. Exhaust slot 78 in the lower, or first, end portion of housing cylinder 16 and opening 80 in top panel 44 provide a flow path from outer annular passageway to enclosure 13 in base housing 12 which serves as plenum for circulating air.

Figure 4:
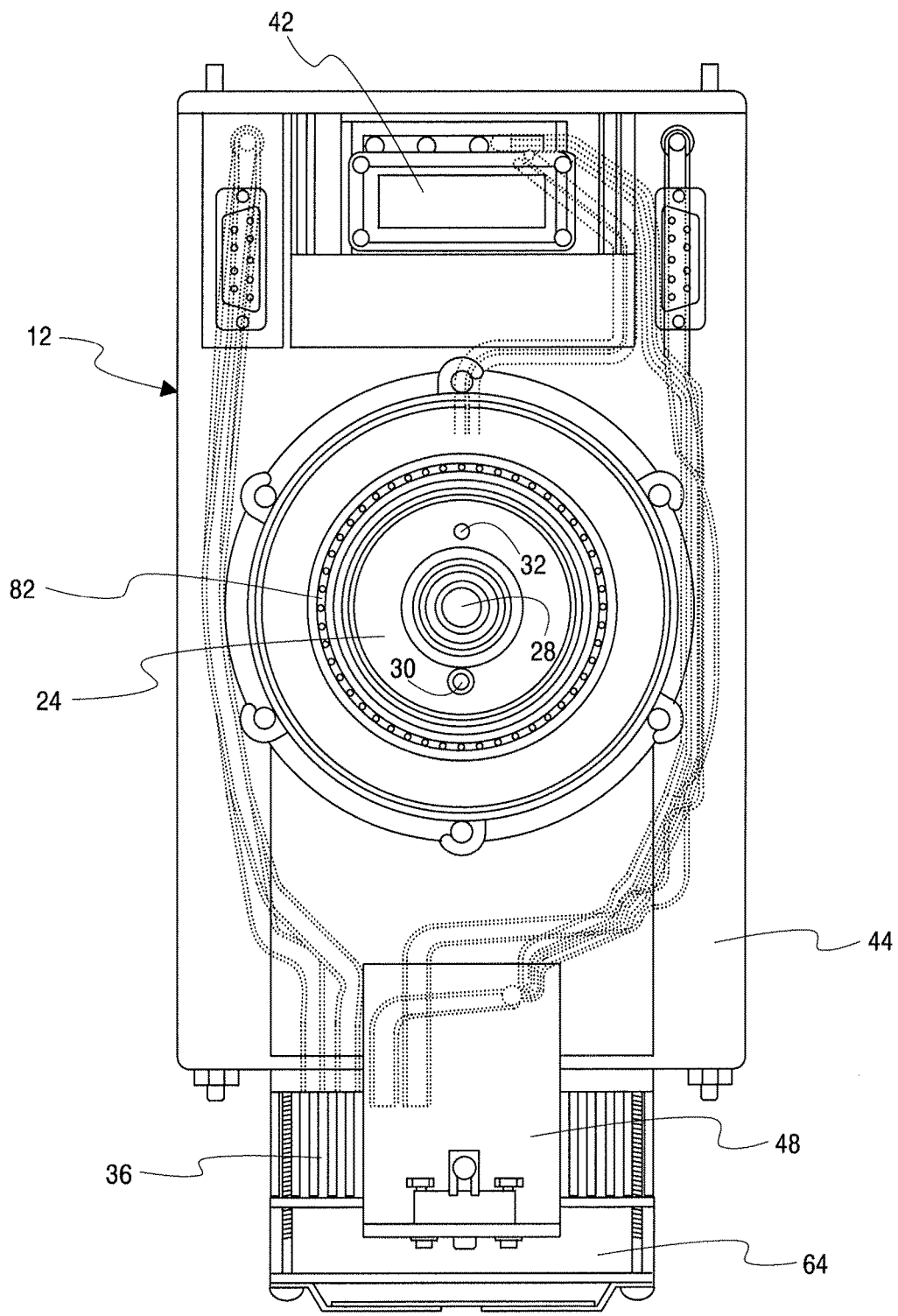
FIG. 4 is a top view of the apparatus shown in FIG. 1.

An optional array of light emitting diodes (LEDs), such as ring of lights 82, is also seated in open socket 72 for sample illumination while camera 49 is operational, if desired (FIGS. 2 and 4). Heat lamp 70 is turned off while camera 49 is on.

Sample cylinder 22 is suspended from housing cylinder cap 20, extends within open-ended transparent cylinder 74, and together with transparent cylinder 74 defines inner annular passageway 84 therebetween. At the upper or proximal end 86 of transparent intermediate cylinder 74 inner annular passageway is in flow communication with and joins outer annular passageway 76. Inner annular passageway 84 is in flow communication with enclosure 13.

Heat lamp 70 in base housing 12 is positioned under conical reflector 68 and below the closed end of sample cylinder 22. Peltier device 66 with external heat exchanger 36 and internal heat exchanger 90 is mounted in rear panel 40 of base housing 12. Air circulation fan 92 in front of internal heat exchanger 90 induces air flow past heat lamp 70 into conical reflector 68 and inner annular passageway 84. Air flow exits inner annular passageway 84 at proximal end 86, enters outer annular passageway 76, and returns to the plenum in base housing 12 through exhaust slot 78 at the lower, or first, end portion of housing cylinder 16 into manifold or duct 96 defined by duct cover 46 and top panel 44, and opening 80 in top panel 44. Preferably, the cross-sectional area of the outer confined flow passageway is greater than the cross-sectional area of the inner confined flow passageway.

Heat lamp 70 can be an incandescent, infrared wavelength emitting light bulb which not only heats the surrounding air by conduction but also radiates heat to the bottom of sample cylinder 20. The spacing between heat lamp 70 and the bottom of sample cylinder 20 preferably is in the range of about 1 to 2½ inches (25 to 63.5 cm), more preferably about 1½ inches (38 cm).

Annular confined flow passageways 76 and 84 together with duct 96, fan 92 and enclosure 13 in base housing 12 provide an efficient and effective closed loop air circulation system which serves to heat a lubricating oil sample in sample cylinder 20 to the desired test temperature and to maintain the sample at the test temperature for duration of the test procedure.

Air pipe 28 carrying diffuser 100 at the distal end of air pipe 28 extends into graduated sample cylinder 22 substantially the entire length thereof. In use, gas diffuser 100 is submerged in the sample to be tested and gas, usually ambient air, is introduced at a predetermined rate and pressure to generate foam in the sample. A temperature sensor such as a thermometer or a thermistor is introduced into graduated sample cylinder 22 via temperature sensor port 30. In FIG. 2, thermistor 102 is shown free standing; however, thermistor 102 can also be carried by gas pipe 28 and positioned in the vicinity of gas diffuser 100.

Air for foam generation is supplied from an external source via air tube 56 (FIG. 1) and through controller-mass flow meter 104 to air tube 28. Vent conduit 32 is in flow communication with mass flow meter 106 which is, in turn, connected to exhaust gas tube 62 by conduit 63. In this manner the existence of a leak in the sparging gas flow can be detected. That is, for a leak-free operation the amount of sparging gas entering the diffuser must be equal the amount of gas leaving the sample cylinder.

Figure 5:
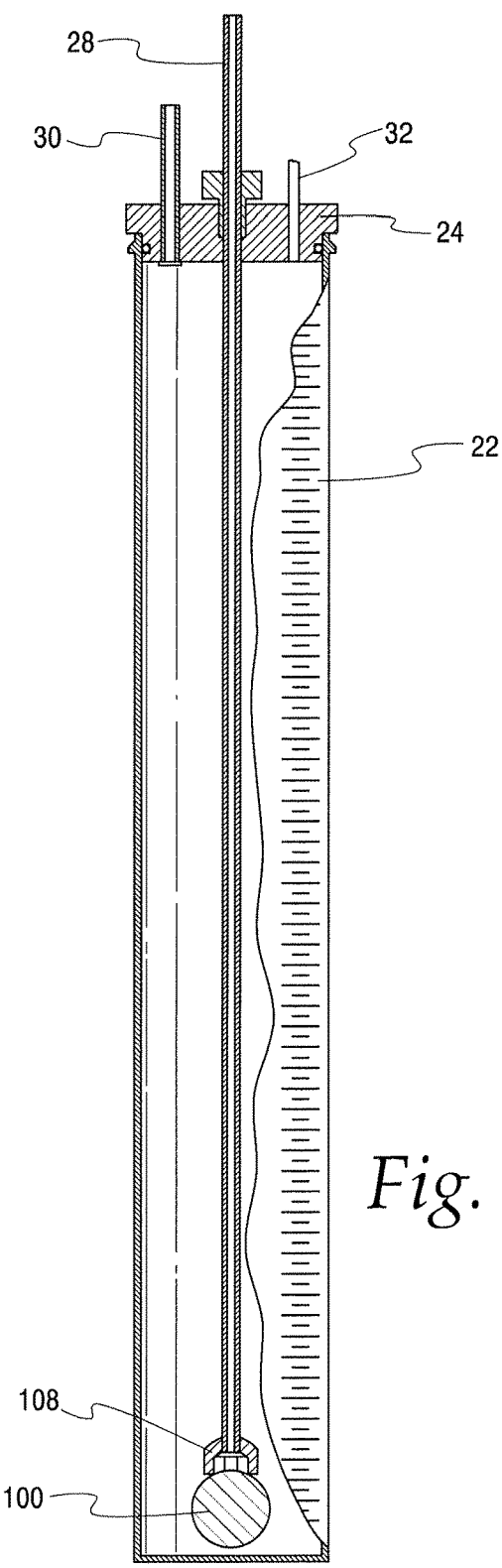
FIG. 5 is a side elevation view, partly in section, of the sample cylinder together with an air pipe and terminal diffuser suitable for use in the foam testing apparatus embodying the present invention.

FIG. 5 illustrates transparent graduated sample cylinder assembly suitable for use with the present foam testing apparatus. Gas diffuser 100, having a spherical shape, is removably mounted at the distal end of gas tube 28 suspended in graduated sample cylinder 22 from sample cylinder cap 24. Diffuser 100 is held in place by diffuser retaining nut 108. The gas diffuser can also have a cylindrical shape, a prismoid shape, and the like as desired.

FIGS. 6 and 7 show a collar 210 that can be used to support the open-ended transparent intermediate cylinder, such as intermediate cylinder 374, in lieu of conical reflector 68 shown in FIG. 2. Collar 210 can be mounted to the base housing in the top opening in the base housing.

Collar 210 defines a central passage 212, a circumferential groove 214, and a peripheral shoulder 216 around the periphery of passage 212. Recess 218 on the underside of collar 210 is adapted to receive a sample illumination device, for example, a ring of LEDs.

Figure 8:
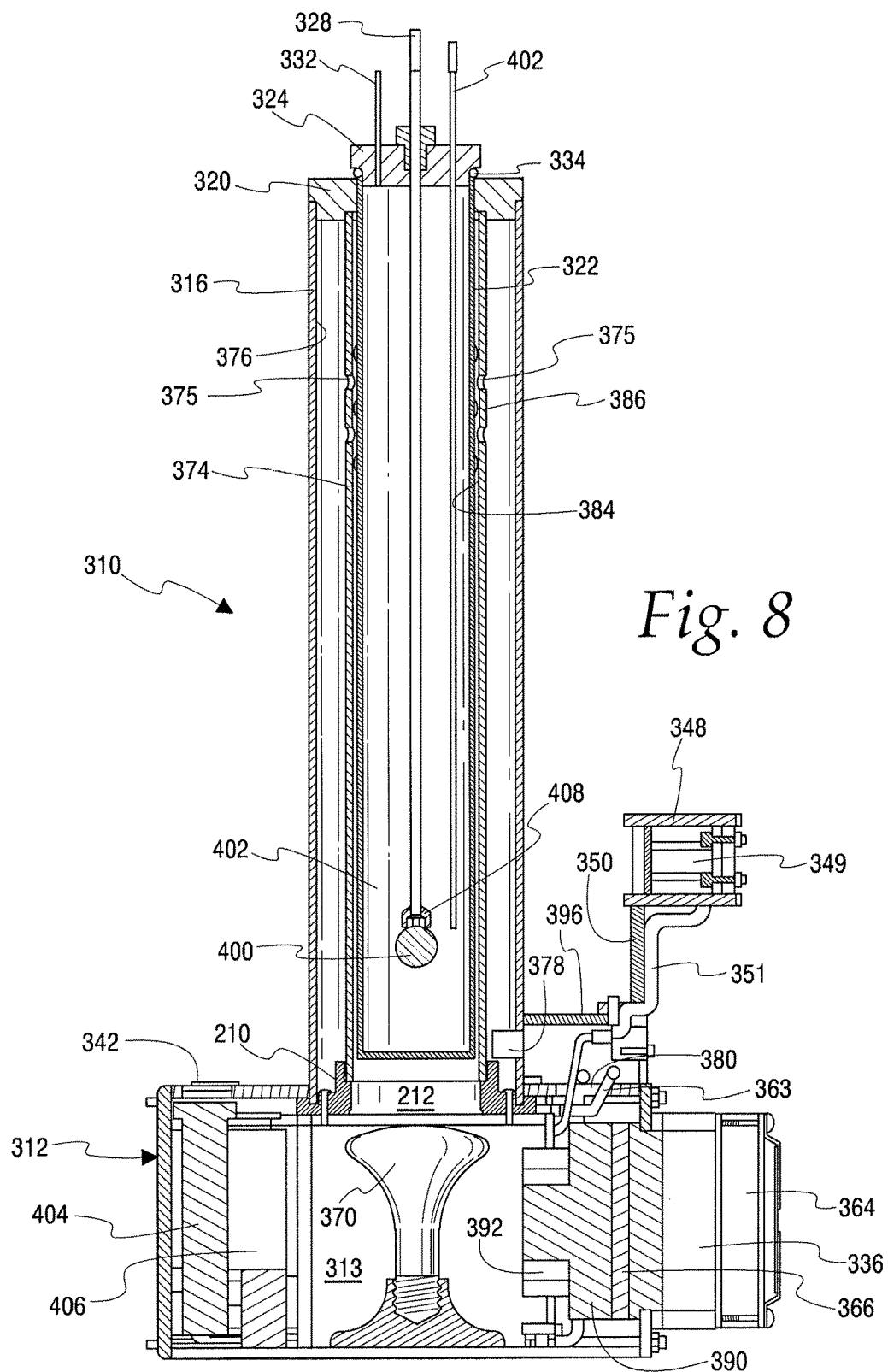
FIG. 8 is a side sectional view of an alternate embodiment of the foam testing apparatus.

Foam testing apparatus provided with a collar for supporting the housing cylinder and the intermediate cylinder is illustrated in FIG. 8.

Referring to FIG. 8, foam testing apparatus 310 is provided with a base housing 312 which defines an enclosure 313 having a top opening 314. Collar 210 is mounted to enclosure 313 in top opening 314 and defines central passage 212. Transparent housing cylinder 316 is open at both ends, and the lower, or first, end portion of housing cylinder 316 is seated in circumferential groove 214 of collar 210. Transparent intermediate cylinder 374 is also open at both ends, but the upper, or second, end portion thereof abuts housing cylinder cap 320. Perforations 375 at the proximal end portion 386 of inner annular confined flow passageway 384 provide flow communication with outer annular confined flow passageway 376. The lower, or first, end portion of intermediate cylinder 374 abuts peripheral shoulder 216 of collar 210.

Housing cylinder cap 320 is received in the upper, or second, end portion of housing cylinder 316 and provides an air-tight seal.

Transparent graduated sample cylinder 322, sealed by sample cylinder cap 324, is received in central aperture 326 defined by housing cylinder cap 320, and is suspended from housing cylinder cap 320. Apertures in sample cylinder cap 324 receive air pipe 328, temperature sensor 402, and vent conduit 332. A sealing gasket, such as o-ring and the like, provides airtight seal between housing cylinder cap 320 and sample cylinder cap 324.

External heat exchanger 336 protrudes outwardly from rear panel 340 of base housing 312. Cooling fan 364 distributes air over external heat exchanger 336. Temperature display window 342 is provided in top panel 344. A duct or manifold 396 provides air flow communication between housing cylinder 316 and enclosure 313 defined by base housing 12. A portion of enclosure 313 serves as plenum for an air circulation system within housing cylinder 316.

Camera housing 348 is mounted adjacent to housing cylinder 316 by camera housing bracket 350. Digital camera 349 is provided in housing 348 for observation and recording of foam characteristics during a foaming test procedure. Camera housing bracket 350 can hold housing 348 in a fixed position relative to transparent housing cylinder 316. Alternatively, bracket 350 can be adjustable, for example using a step motor (not shown), along housing cylinder 316.

Camera cable 351 connects digital camera 349 within camera housing 348 to an image processing unit and digital signal processor (not shown) within base housing 312.

Connection to an external power source for an air circulation fan, a cooling fan, controller, flow meter, mass flow meter, microprocessor, and the like, as well as for a heat lamp, LED illumination of sample, and the like, is provided by a power socket equipped with a fuse in a manner similar to that shown in FIG. 2.

Peltier device 366 within base housing 312 provides thermoelectric cooling for circulated air.

External heat exchanger 336 and associated fans 364 are on the hot side of Peltier device 366. Internal heat exchanger 390 with associated air circulation fan 392 are on the cold side of Peltier device 366. Heat lamp 370 and Peltier device 366 are in enclosure 313 adjacent to one another and in the path of an air stream circulated through enclosure 313.

Peltier device 366 primarily serves to decrease temperature of circulating air as stated hereinabove. Peltier device 366 can also supply additional heat to the circulating air by reversing the direction of current, if desired. In such a case, the normally cold side of Peltier device becomes its hot side, and vice versa.

An outer annular confined flow passageway 376 is defined between transparent housing cylinder 316 and transparent intermediate cylinder 374. Exhaust slot 378 in the lower end portion of housing cylinder 316 and opening 380 in base housing top panel 340 provide a flow path from outer annular confined flow passageway 376 to enclosure 313 in base housing 312.

An optional array of light emitting diodes (LEDs), such as ring of LEDs, can be mounted in recess 218 of collar 210 for sample illumination while camera 349 is operational, if desired. Heat lamp 370 is turned off while camera 349 is on.

Sample cylinder 322 is suspended from housing cylinder cap 320, extends within open-ended transparent cylinder 374, and together with transparent intermediate cylinder 374 defines inner annular confined flow passageway 384 therebetween. At the upper, or second, end portion of transparent intermediate cylinder 374, inner annular passageway is in flow communication with and joins outer annular passageway 376 through perforations 375 in intermediate cylinder 374. Inner annular passageway 384 also is in flow communication with enclosure 313.

Heat lamp 370 in base housing 312 is positioned below the closed end of sample cylinder 322. Peltier device 366 with external heat exchanger 336 and internal heat exchanger 390 is mounted in rear panel 340 of base housing 312. Air circulation fan 392 in front of internal heat exchanger 390 induces air flow past heat lamp 370, through passage 212, and into inner annular passageway 384. Air flow exits inner annular passageway 384 at proximal end 386 through perforations 375, enters outer annular passageway 376, and returns to the plenum in base housing 312 through exhaust slot 378 at the lower, or first, end portion of housing cylinder 316 into manifold 396, and opening 380 in top panel 344. Preferably, the cross-sectional area of the outer confined flow passageway is greater than the cross-sectional area of the inner confined flow passageway. If intermediate cylinder 374 does not extend to housing cylinder cap 320, perforations 375 at the upper end portion of intermediate cylinder 374 can be omitted.

Heat lamp 370 can be an incandescent, infrared wavelength emitting light bulb which not only heats the surrounding air by conduction but also radiates heat to the bottom of sample cylinder 320. The spacing between heat lamp 370 and the bottom of sample cylinder 320 preferably is in the range of about 1 to 2½ inches (25 to 63.5 cm), more preferably about 1½ inches (38 cm).

Annular confined flow passageways 376 and 384 together with duct 396, fan 392 and enclosure 313 in base housing 312 provide an efficient and effective closed loop air circulation system for heating a lubricating oil sample in sample cylinder 320 to the desired test temperature. The sample is maintained at the test temperature for duration of the test procedure.

Air pipe 328 carrying diffuser 400 at the distal end of air pipe 328 extends into graduated sample cylinder 322 substantially the entire length thereof. In use, gas diffuser 400 is submerged in the sample to be tested and a gas, usually ambient air, is introduced at a predetermined rate and pressure to generate foam in the sample. Gas diffuser 400 is held in place by retaining nut 408. A temperature sensor such as a thermometer or a thermistor 402 is introduced into graduated sample cylinder 322 via temperature sensor port 330. Thermistor 402 is shown free standing; however, thermistor 402 can also be carried by air pipe 328 and positioned in the vicinity of gas diffuser 400.

Air for foam generation is supplied from an external source in the same manner as described for the embodiment of this invention illustrated by FIGS. 2-5, hereinabove.

The foam testing apparatus described herein is well suited for performing ASTM D892-13 Standard Test Method for Foaming characteristics of Lubricating Oils, the description of which is incorporated herein by reference.

The gas diffuser suitable for the present foam testing apparatus can be spherical or cylindrical. Gas diffusers can be fabricated from ceramics or metal. Typical spherical gas diffuser stones are made of fused crystalline alumina grains such as those commercially available from Norton Co., Worcester, Mass. Typical cylindrical gas diffusers made of metal are made of sintered porous stainless steel such as those commercially available from Petrolab Corporation, Latham, N.Y.

Suitable gas diffusers have maximum pore diameters of <80 μm and air permeability in the range of 3,000 to 6,000 milliliters per minute at a pressure differential of 250 mm water.

The foregoing description and the drawings are illustrative of the present invention and are not to be taken as limiting. Still other variants within the spirit and scope of this invention are possible and will readily present themselves to those skilled in the art.

The invention claimed is:

1. A foam testing apparatus which comprises
   a base housing defining an enclosure and having a top opening;
   a transparent housing cylinder, having first and second open end portions, the first open end portion being mounted to the base housing over said top opening;
   a transparent intermediate cylinder having first and second open end portions, within the transparent housing cylinder and together with the transparent housing cylinder defining an outer annular confined flow passageway therebetween;
   a heat lamp in said enclosure under the first open end portion of the transparent housing cylinder;
   a housing cylinder cap in the second open end portion of the transparent housing cylinder and defining a central aperture;
   an elongated, transparent sample cylinder having a closed bottom and an open top portion received in the central aperture, extending into the open ended, transparent intermediate cylinder, and defining an inner annular confined flow passageway therebetween;
   a sample cylinder cap received in the open top portion of the sample cylinder and defining a vent;
   a temperature sensor in the sample cylinder;
   a gas pipe carried by the sample cylinder cap and extending into the sample cylinder substantially along the entire length of the sample cylinder;
   a gas diffuser at a distal end of the gas pipe; and
   a fan in the enclosure adapted to circulate gas through the confined flow passageways;
   said second open end portion of the housing cylinder defining an exhaust slot for flow communication with the enclosure.

2. The foam testing apparatus in accordance with claim 1 which includes a camera positioned adjacent to the transparent housing cylinder for recording appearance of foam generated in the sample cylinder.

3. The foam testing apparatus in accordance with claim 1 wherein the heat lamp is an incandescent infrared wavelength light emitting bulb.

4. The foam testing apparatus in accordance with claim 1 wherein the cross-sectional area of the outer confined flow passageway is greater than the cross-sectional area of the inner confined flow passageway.

5. The foam testing apparatus in accordance with claim 1 wherein an array of light-emitting diodes is present in the open socket.

6. The foam testing apparatus in accordance with claim 1 wherein the gas diffuser has a spherical shape.

7. The foam testing apparatus in accordance with claim 1 wherein the heat lamp and an adjacent Peltier device are situated in the enclosure in a heat exchange relationship with an air stream passing through the enclosure.

8. The foam testing apparatus in accordance with claim 1 wherein the second open end portion of the transparent intermediate cylinder is perforated.

9. A foam testing apparatus which comprises
a base housing defining an enclosure and having a top opening;
a collar mounted to the enclosure around said opening, defining a central passage, an internal shoulder around the passage, and an outer circumferential groove;
a transparent housing cylinder having first and second open end portions, the first open end portion being received in the circumferential groove of said collar;
an open ended transparent intermediate cylinder within the transparent housing cylinder, having first and second open end portions, having the first end portion of the transparent intermediate cylinder abutting the internal shoulder of the collar, and together with the transparent housing cylinder defining an outer confined flow passageway therebetween;
a heat lamp in said enclosure under the first open end portion of the transparent housing cylinder;
a housing cylinder cap in the second open end portion of the transparent housing cylinder and defining a central aperture;
an elongated, transparent sample cylinder having a closed bottom and an open top portion received in the central aperture, extending into the open ended, transparent intermediate cylinder, and defining an inner annular confined flow passageway therebetween;
a sample cylinder cap received in the open top portion of the sample cylinder and defining a vent;
a temperature sensor in the sample cylinder;
a gas pipe carried by the sample cylinder cap and extending into the sample cylinder substantially along the entire length of the sample cylinder;
a gas diffuser at a distal end of the gas pipe; and
a fan in the enclosure adapted to circulate gas through the confined flow passageways;
said second open end portion of the housing cylinder defining an exhaust slot for flow communication with the enclosure.

10. The foam testing apparatus in accordance with claim 9 which includes a camera positioned adjacent to the transparent housing cylinder for recording appearance of foam generated in the sample cylinder.

11. The foam testing apparatus in accordance with claim 9 wherein the heat lamp is an incandescent infrared wavelength light emitting bulb.

12. The foam testing apparatus in accordance with claim 9 wherein the cross-sectional area of the outer confined flow passageway is greater than the cross-sectional area of the inner confined flow passageway.

13. The foam testing apparatus in accordance with claim 9 wherein an array of light-emitting diodes is present in the open socket.

14. The foam testing apparatus in accordance with claim 9 wherein the gas diffuser has a spherical shape.

15. The foam testing apparatus in accordance with claim 9 wherein the heat lamp and an adjacent Peltier device are situated in the enclosure in a heat exchange relationship with an air stream passing through the enclosure.

16. A foam testing apparatus which comprises:
a base housing defining an enclosure and having a top opening;
a transparent housing cylinder, having first and second open end portions, the first open end portion being mounted to the base housing over said top opening;
a heat lamp in said enclosure under the first open end portion;
a conical reflector within the first open end portion, situated over the heat lamp, and defining an upstanding open socket;
an open ended transparent cylinder received in the socket and together with the housing cylinder defining an outer annular confined flow passageway therebetween;
a housing cylinder cap in the second open end portion of the housing cylinder and defining a central aperture;
an elongated, transparent sample cylinder having a closed bottom and an open top portion received in the central aperture, extending into the open-ended transparent cylinder and defining an inner annular confined flow passageway therebetween;
a sample cylinder cap received in the open top portion of the sample cylinder and defining a vent;
a temperature sensor in the sample cylinder;
a gas pipe carried by the sample cylinder cap and extending into the sample cylinder substantially along the entire length of the sample cylinder;
a gas diffuser at distal end of the gas pipe; and
a fan in the enclosure adapted to circulate gas through the confined flow passageways;
said second open end portion of the housing cylinder defining an exhaust slot for flow communication with the enclosure.

17. The foam testing apparatus in accordance with claim 16 which includes a camera positioned adjacent to the transparent housing cylinder for recording appearance of foam generated in the sample cylinder.

18. The foam testing apparatus in accordance with claim 16 wherein the heat lamp is an incandescent infrared wavelength light emitting bulb.

19. The foam testing apparatus in accordance with claim 16 wherein the cross-sectional area of the outer confined flow passageway is greater than the cross-sectional area of the inner confined flow passageway.

20. The foam testing apparatus in accordance with claim 16 wherein an array of light-emitting diodes is present in the open socket.

* * * * *